(12) United States Patent
Worthley

(10) Patent No.: US 6,706,940 B2
(45) Date of Patent: Mar. 16, 2004

(54) TRANSPARENT FILM DRESSING AND A METHOD FOR APPLYING AND MAKING THE SAME

(75) Inventor: George Worthley, Wheaton, IL (US)

(73) Assignee: George Medical, L.L.C., Wheaton, IL (US)

( * ) Notice: Subject to any disclaimer, the term of this patent is extended or adjusted under 35 U.S.C. 154(b) by 340 days.

(21) Appl. No.: 09/892,057

(22) Filed: Jun. 26, 2001

(65) Prior Publication Data

US 2002/0115954 A1 Aug. 22, 2002

Related U.S. Application Data

(60) Provisional application No. 60/270,291, filed on Feb. 22, 2001.

(51) Int. Cl.$^7$ ................................................ A61F 13/00
(52) U.S. Cl. .............................. 602/57; 602/42; 602/54; 602/58
(58) Field of Search ................................. 128/888, 889; 602/41–59; 604/290, 304–308

(56) References Cited

U.S. PATENT DOCUMENTS

| | | |
|---|---|---|
| 3,991,754 A | 11/1976 | Gertzman |
| 4,413,621 A | 11/1983 | McCracken et al. |
| 4,485,809 A | 12/1984 | Dellas |
| 4,513,739 A | 4/1985 | Johns |
| 4,598,004 A | 7/1986 | Heinecke |
| 4,614,183 A | 9/1986 | McCracken et al. |
| 4,664,106 A | 5/1987 | Snedeker |
| 4,669,458 A | 6/1987 | Abraham et al. |
| 4,678,462 A | 7/1987 | Vaillancourt |
| 4,753,231 A | 6/1988 | Lang et al. |
| 4,753,232 A | 6/1988 | Ward |
| 4,787,380 A | 11/1988 | Scott |
| 4,815,457 A | 3/1989 | Mazars et al. |
| 4,875,473 A | 10/1989 | Alvarez |
| 4,884,563 A | 12/1989 | Sessions |
| 4,915,102 A | 4/1990 | Kwiatek et al. |
| 4,917,112 A | 4/1990 | Kalt |
| 4,926,850 A | 5/1990 | Lott et al. |
| RE33,353 E | 9/1990 | Heinecke |
| 5,000,172 A | 3/1991 | Ward |
| 5,012,801 A | 5/1991 | Feret |
| 5,018,516 A | 5/1991 | Gilman |
| 5,035,687 A | 7/1991 | Sandbank |
| 5,042,466 A | 8/1991 | McKnight |
| 5,052,381 A | 10/1991 | Gilbert et al. |
| 5,074,293 A | 12/1991 | Lott et al. |
| 5,092,323 A | 3/1992 | Riedel et al. |
| 5,099,832 A | 3/1992 | Ward |
| 5,106,629 A | 4/1992 | Cartmell et al. |
| 5,152,282 A | 10/1992 | Elphick et al. |
| 5,153,040 A | 10/1992 | Faasse, Jr. |
| 5,160,315 A | 11/1992 | Heinecke et al. |
| 5,188,124 A | 2/1993 | Feret |
| 5,266,371 A | 11/1993 | Sugii et al. |
| 5,333,753 A * | 8/1994 | Etheredge .................... 221/33 |

(List continued on next page.)

Primary Examiner—Kim M. Lewis
(74) Attorney, Agent, or Firm—Patents+TMS, P.C.

(57) ABSTRACT

A transparent film dressing for wounds and intravenous catheter sites and a method for applying such a dressing and a process for making the same are provided. The film dressing has a top layer optionally printed with a measuring guide. The top layer acts as a casting sheet for the second layer of a moisture vapor permeable film. The moisture vapor permeable film may be coated with an adhesive and covered with a silicone coated protective paper or film. The film dressing may also have a tab and/or gripping strip for removal of layers and/or application of the dressing to a patient. The film dressing may be applied to the patient with the top layer printed with a the measuring guide. Alternatively, the top layer may be removed.

12 Claims, 3 Drawing Sheets

U.S. PATENT DOCUMENTS

| | | |
|---|---|---|
| 5,372,589 A | 12/1994 | Davis |
| 5,415,627 A * | 5/1995 | Rassmussen et al. ......... 602/57 |
| 5,512,041 A | 4/1996 | Bogart |
| 5,520,629 A | 5/1996 | Heinecke et al. |
| 5,628,724 A | 5/1997 | DeBusk et al. |
| 5,643,187 A | 7/1997 | Naestoft et al. |
| 5,722,943 A | 3/1998 | Sessions |
| 5,738,642 A | 4/1998 | Heinecke et al. |
| 5,755,681 A | 5/1998 | Plews |
| 5,785,690 A | 7/1998 | Newman et al. |
| 5,792,089 A | 8/1998 | Penrose et al. |
| 5,840,052 A | 11/1998 | Johns |
| 5,891,078 A | 4/1999 | Turngren et al. |
| 5,931,800 A | 8/1999 | Rasmussen et al. |
| 5,968,000 A | 10/1999 | Harrison et al. |
| 5,998,694 A | 12/1999 | Jensen et al. |
| 6,008,429 A | 12/1999 | Ritger |
| 6,019,996 A | 2/2000 | Cheong |
| 6,043,406 A | 3/2000 | Sessions et al. |
| 6,093,465 A | 7/2000 | Gilchrist et al. |
| 6,124,520 A | 9/2000 | Roberts |
| 6,124,521 A | 9/2000 | Roberts |
| 6,140,548 A | 10/2000 | Hansen et al. |
| 6,350,339 B1 * | 2/2002 | Sessions .................... 156/250 |

* cited by examiner

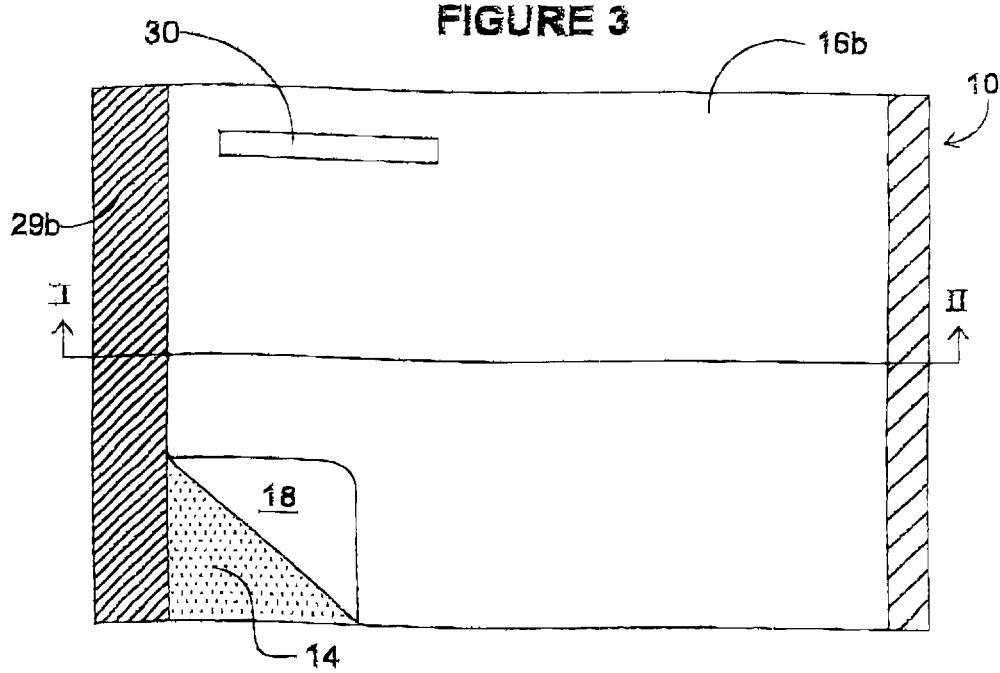
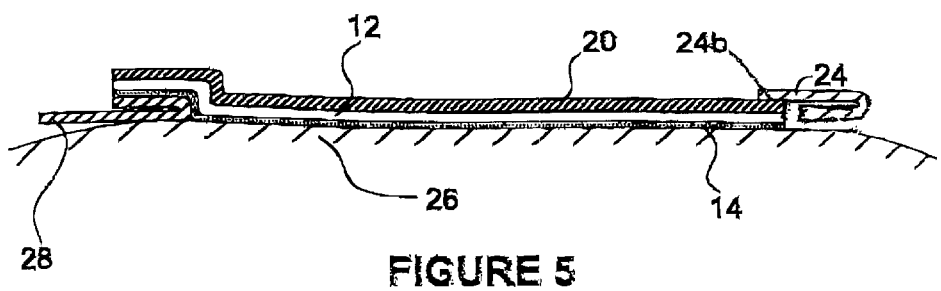
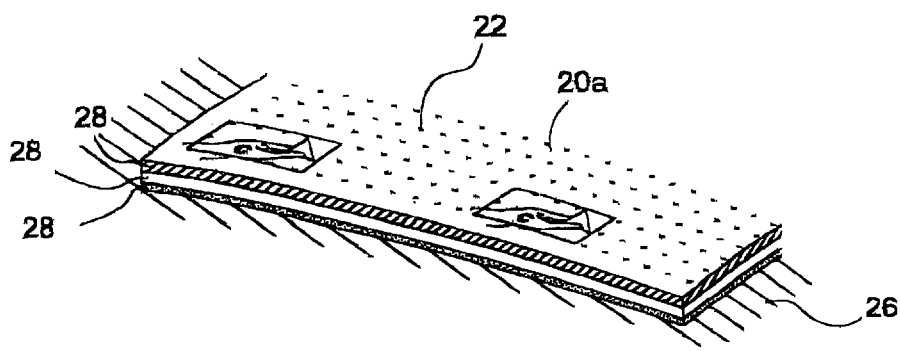

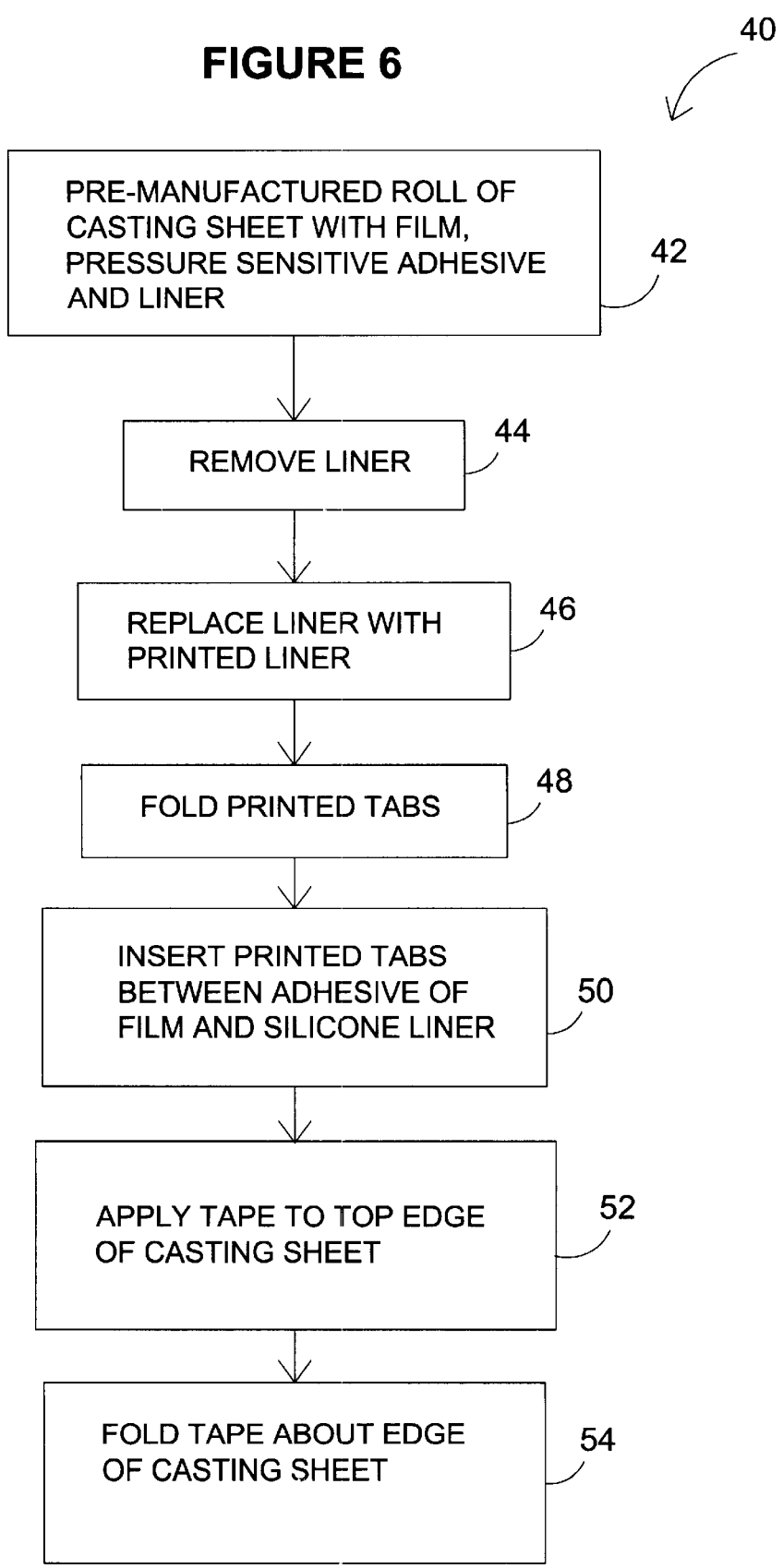

TRANSPARENT FILM DRESSING AND A METHOD FOR APPLYING AND MAKING THE SAME

This application claims the benefit of U.S. Provisional Application Serial No.: 60/270,291 filed Feb. 22, 2001.

BACKGROUND OF THE INVENTION

The present invention generally relates to a transparent film dressing for wounds and/or intravenous catheter sites as well as a method for applying such a dressing and a process for making the same. More specifically, the present invention relates to a film dressing having a substantially clear top layer that may be printed with a dot matrix measuring guide. The top layer may provide a casting sheet for a moisture vapor permeable film. The moisture vapor permeable film may be coated with an adhesive and may be covered with a silicon-coated protective paper or film. The film dressing may have a tab and/or gripping strip for removal of layers and application of the dressing to a patient. The film dressing of the present invention may be placed in a pouch and may be sterilized for use on a patient.

It is, of course, generally known to use transparent film dressings for the treatment and/or covering of wounds and intravenous catheter sites. Wound dressings that are adhered to human skin by pressure-sensitive adhesive have been known for many years. Such dressings are generally in the form of a sheet of film, foam, fabric or combination thereof. Known sheets have a pressure-sensitive adhesive layer for adhering the dressing to skin adjacent to the wound to secure the dressing in place. The pressure-sensitive adhesive layer may be configured to adhere to the skin surrounding the wound or to portions of skin surrounding the wound. In many dressings, the adhesive layer is substantially coextensive with the dressing and thus extends over the wound itself. In such dressings, the adhesives are intended to adhere to healthy skin outside the wound but not to the wound itself. The adhesives do not adhere to the wound itself due to the inherent moisture of wounds.

A problem associated with these dressings include layers of the film dressing that stick to each other. Another problem associated with these dressings include adhesive oozing into score lines of casting sheets and/or score lines of the film, foam, or fabric sheet. For example, when applying a film dressing with score lines, after a scored portion of a layer is removed, adhesive may ooze into the score line. Yet another problem associated with these dressings include the dressings being difficult to use and/or apply. For example, when using a film dressing, the layers of the film dressing may wrinkle or stick together making the dressing difficult to apply.

A need, therefore, exists for a transparent film dressing for wounds and/or intravenous catheter sites and a method for applying such a dressing and a process for making the same.

SUMMARY OF THE INVENTION

The present invention generally relates to a transparent film dressing for wounds and intravenous catheter sites and a method for applying such a dressing and a process for making the same.

To this end, in an embodiment of the present invention, a dressing is provided having a transparent film having an adhesive coating, a liner having a non adhesive coating, a casting sheet, a gripping strip and a hinge. The transparent film has a top side, a bottom side, a left edge and a right edge. The adhesive coating is located on the bottom side of the transparent film. The liner having the non-adhesive coating is removably attached to the adhesive coating on the bottom side of the transparent film. The casting sheet has a top surface defined by a peripheral edge, and the casting sheet is releasably attached to the top side of the transparent film. The gripping strip is attached to the casting sheet. The hinge is removably attached to the liner and removably attached to the transparent film at a distance from the left edge.

In an embodiment, the hinge of the dressing is folded such that a portion of the hinge is removably attached to the adhesive coating.

In an embodiment, the gripping strip of the dressing extends beyond the peripheral edge of the top surface of the casting sheet and folds around the casting sheet such that the gripping strip is adjacent to the adhesive coating.

In an embodiment, the dressing has instructions printed on the liner.

In an embodiment, the casting sheet of the dressing is constructed of polyethylene and/or a blend of polypropylene and polyethylene.

In an embodiment, the transparent film of the dressing is moisture vapor permeable.

In an embodiment, the dressing has a pattern on the casting sheet.

In an embodiment, the gripping strip of the dressing is constructed of cellophane tape.

In an embodiment, the adhesive coating of the dressing extends from the left edge of the transparent film to the right edge of the transparent film such that the adhesive coating is adjacent to the gripping strip.

In an embodiment, the adhesive coating has a pattern.

In an embodiment, the dressing has information printed on the hinge.

In another embodiment of the present invention, a method of applying a dressing to a patient is provided. The method comprises the steps of: providing a film having a top side and a bottom side; providing the bottom side of the film with an adhesive; providing a liner having a non-adhesive coating removably attached to the adhesive coating; providing a casting sheet releasably attached to the top side of the film wherein the casting sheet has a top surface; providing a gripping strip attached to the top surface of the casting sheet; providing a hinge; holding the hinge; removing the liner; holding the gripping strip and the hinge; applying the casting sheet, the film, and the adhesive to the patient; and removing the hinge.

In an embodiment, the method of applying a dressing to a patient further comprises the step of removing the casting sheet from the film.

In an embodiment, the method of applying a dressing to a patient further comprises the step of providing a pattern on the casting sheet.

In another embodiment of the present invention, a process for manufacture of a dressing is provided. The process comprises the steps of: providing a roll having a casting sheet, a film, a pressure sensitive adhesive and a liner; providing a tab; providing tape; folding the tab; inserting the folded tab between the film and the pressure sensitive adhesive; applying the tape to the casting sheet; folding the tape around the casting sheet; and applying the tape to the casting sheet.

In an embodiment, the process for manufacture of a dressing further comprises the step of inserting the folded tab between the film and the pressure sensitive adhesive.

In an embodiment, the process for manufacture of a dressing further comprises the step of printing instructions on the tab.

In an embodiment, the process for manufacture of a dressing further comprises the step of printing instructions on the liner.

In an embodiment, the process for manufacture of a dressing further comprises the step of printing the casting sheet with a pattern.

It is, therefore, an advantage of the present invention to provide a dressing, a method for applying a dressing and a process for making the same to cover a wound and/or a catheter site.

Another advantage of the present invention is to provide a dressing, a method for applying a dressing and a process for making the same that promotes moist wound healing.

Another advantage of the present invention is to provide a dressing, a method for applying a dressing and a process for making the same wherein the dressing is easier to use and manufacture.

Yet another advantage of the present invention is to provide a dressing, a method for applying a dressing and a process for making the same wherein the dressing may be produced at a high rate of speed and/or less expensive to manufacture.

Another advantage of the present invention is to provide a dressing, a method for applying a dressing and a process for making the same wherein instructions are printed on the delivery tab of the dressing.

Still further, an advantage of the present invention is to provide a dressing, a method for applying a dressing and a process for making the same wherein printing on the top clear layer of the dressing acts as a guide for tracing and/or measuring the wound covered by the dressing.

Another advantage of the present invention is to provide a dressing, a method for applying a dressing and a process for making the same wherein colored printing is provided on a top clear layer to aid in identification the size of the dressing.

Yet another advantage of the present invention is to provide a dressing, a method for applying a dressing and a process for making the same wherein a tab of the dressing is designed such that removal of the casting sheet from the top of the moisture vapor permeable film layer may be accomplished without touching the adhesive coating or film layer.

Additional features and advantages of the present invention are described in, and will be apparent from, the detailed description of the presently preferred embodiments and from the drawings.

BRIEF DESCRIPTION OF THE DRAWINGS

FIG. 3 is a back plan view of an embodiment of a dressing of the present invention.

FIG. 4 is a cross-sectional view taken generally along the line II—II of FIG. 3 of an embodiment of a dressing of the present invention.

FIG. 5 is a perspective view of an embodiment of a dressing of the present invention FIG. 6 is a flowchart illustrating an embodiment of a method of making a dressing.

DETAILED DESCRIPTION OF THE PRESENTLY PREFERRED EMBODIMENTS

The present invention generally relates to a transparent film dressing for wounds and intravenous catheter sites and a method for applying and making the same.

Figure 1:
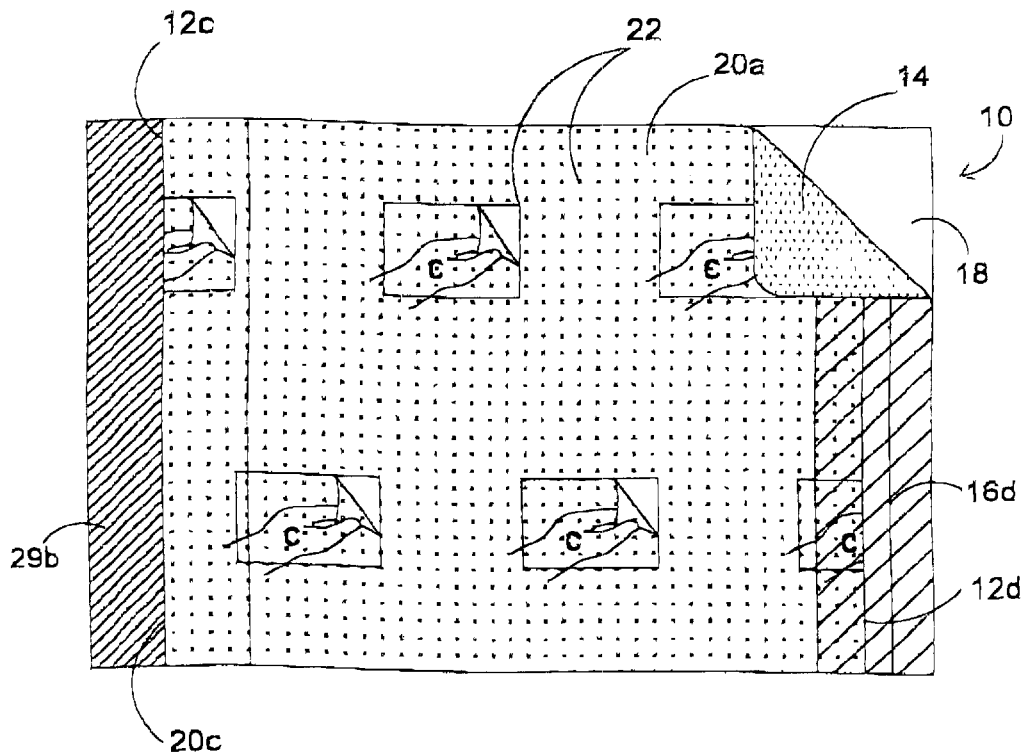
FIG. 1 is a front plan view of an embodiment of a dressing of the present invention.
Figure 2:
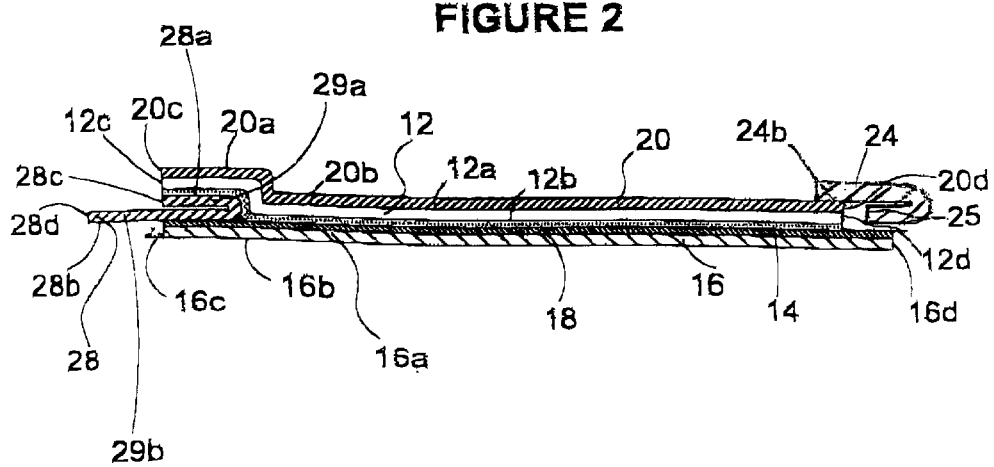
FIG. 2 is a cross-sectional view taken generally along the line II—II of FIG. 3 of an embodiment of a dressing of the present invention.

Referring now to the drawings wherein like numerals refer to like parts, FIGS. 1, 2 and 3 illustrate a dressing 10 of the present invention. As shown in FIGS. 1, 2 and 3, the dressing 10 may have a number of layers and tabs. More specifically, the dressing may have a casting sheet 20, a transparent film 12 with an adhesive coating 14, a liner 16 with a non-adhesive coating 18, a gripping strip 24 and a hinge 28.

The transparent film 12 may have a top side 12a, a bottom side 12b, a left edge 12c and a right edge 12d. Preferably, the transparent film may be constructed of polyurethane and/or is moisture vapor permeable. The adhesive coating 14 of the transparent film 12 may substantially cover the bottom side 12b of the transparent film 12. Alternatively, the adhesive coating 14 may have a pattern (not shown) such that a portion of the bottom side 12b of the transparent film 12 is covered by the adhesive coating 14.

The liner 16 may have a top surface 16a and a bottom surface 16b. The non-adhesive coating 18 may be located on the top surface 16a of the liner 16 and may be removably attached to the adhesive coating 14. The non-adhesive coating 18 may be constructed of, for example, silicone. Further, instructions 30 may be printed on the bottom surface 16d of the liner 16. Instructions 30 may include, for example, to remove the liner first when applying the dressing. Alternatively, the instructions 30 may be printed as part of a pattern that may cover a portion or all of the bottom surface 16b of the liner 16.

The casting sheet 20 may have a right side 20a and a left side 20b and may be releasably attached to the top side 12a of the transparent film 12. In a preferred embodiment, the casting sheet 20 may be constructed of polypropylene and/or a blend of polypropylene and polyethylene for more flexibility. Further, the casting sheet 20 may have a printed pattern 22. For example, the printed pattern 22 may be a dot pattern. Preferably, the dot pattern has a distance of 2.5 mm between adjacent dots. However, the dot pattern may have a distance between adjacent dots ranging from 1 mm to 20 mm depending on the size of the wound, shape of the wound, the size of the wound dressing used and/or any other factor(s) associated with tracing and/or measuring the wound and/or the particular applications for use of the dressing.

The printed pattern 22 may be used, for example, to trace and/or measure the wound. To this end, for example, a user may use a pen to connect dots that surround the wound to identify size and/or shape of the wound or may identify specific characteristics of the wound. In addition, the printed pattern 22 may be different colors to indicate, for example, the size of the dressing 10. For example, the printed pattern 22 printed in, for example, the color red, may indicate a small size dressing; similarly, the printed pattern 22 printed in, for example, the color blue, may indicate a medium size dressing.

As shown in FIG. 2, the gripping strip 24 may be attached to the casting sheet 20. An end 25 of the gripping strip 24 may be adjacent to the right side 20d of the casting sheet 20. The end 25 of the gripping strip 24 may also be located adjacent to the right edge 12d of the transparent film 12.

Accordingly, the gripping strip 24 may be placed on the dressing such that the amount of adhesive coating 14 that may be exposed is minimized. The gripping strip 24 may be formed, for example, from cellophane tape.

As further shown in FIG. 2, the hinge 28 may have a top side 28a, a bottom side 28b, a first end 28c and a second end 28d and may be removably attached to the transparent film 12 and the liner 16. A first portion 29a of the hinge 28 may be removably attached to the transparent film 12 at a distance from the left edge 12c of the transparent film 12. The hinge 28 may be folded onto itself such that the first portion 29a of the hinge 28 may be removably attached to the adhesive coating 14. A second portion 29b of the hinge 28 may extend between the first portion 29a of the hinge 28 and the liner 16. The second portion 29b of the hinge 28 may extend at a distance beyond a side edge 16c of the liner 16. Extending the second portion 29b of the hinge 28 a distance beyond the width of the liner 16 and/or transparent film 12 may allow for printing on the hinge 28. Further, in an embodiment, the hinge 28 may be printed with instructions (not shown). Instructions on the hinge may include, for example, to remove the hinge second after removing the liner when applying the dressing.

To use or otherwise apply the dressing 10 to a patient 26, an individual may hold the hinge 28 and may peel back the liner 16 to remove the same. After the liner 16 is removed, the individual may hold the gripping strip 24 and/or the hinge 28 and apply the exposed adhesive coating 14 of the transparent film 12 to a wound and/or catheter site of a patient 26 as shown in FIG. 4.

After applying the exposed adhesive coating 14 of the transparent film 12 to the patient 26, the individual may remove the hinge 28. Accordingly, the casting sheet 20 and the transparent film 12 with the adhesive coating 14 may be applied to the patient 26. The individual may initiate removal of the casting sheet 20 by use of the gripping strip 16 and remove the casting sheet 20 from the transparent film 12 attached to the patient 26. Alternatively, the individual may leave the casting sheet 20 attached to the transparent film 12 to measure and/or trace the wound as shown in FIG. 5. Alternatively, the dressing 10 may be applied by the patient 26.

A flowchart illustrating an embodiment of a method to manufacture the dressing 10 of the present invention is generally illustrated in FIG. 6. A pre-manufactured roll of casting sheet with polyurethane film and/or moisture vapor permeable film, pressure sensitive adhesive and liner having a non-adhesive coating may be used as shown in step 42. The liner of the roll 42 may be removed and may be replaced with a new liner having instructions printed thereon as generally shown at steps 44 and 46, respectively. The instructions may include, for example, to remove the liner first when applying the dressing.

Printed tabs may be folded as shown at step 48 and inserted between the adhesive of the film and the silicone of the liner, as shown at step 50. The folded printed tabs may be used as hinges as described above. Tape may be applied to the top edge of the casting sheet, as shown at step 52. After applying the tab to the casting sheet, the tape may be folded around an edge of the casting sheet as shown at step 54 and as described above. The tape acts as a second tab or gripping strip as described above. No further measuring or scoring of the dressing is required to implement the use of the dressing for application to a patient.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A dressing comprising:

a transparent film having a top side, a bottom side, a left edge and a right edge;

an adhesive coating on the bottom side of the transparent film;

a liner having a non-adhesive coating removably attached to the adhesive coating on the bottom side of the transparent film;

a casting sheet releasably attached to the top side of the transparent film wherein the casting sheet has a top surface defined by a peripheral edge;

a gripping strip attached to the casting sheet; and a hinge removably attached to the transparent film at a distance from the left edge and is further removably attached to the liner.

2. The dressing of claim 1 wherein the hinge is folded such that a portion of the hinge is removably attached to the adhesive coating.

3. The dressing of claim 1 wherein the gripping strip extends beyond the peripheral edge of the top surface of the casting sheet and is folded toward the casting sheet.

4. The dressing of claim 1 further comprising:

instructions printed on the liner.

5. The dressing of claim 1 wherein the casting sheet is constructed of polyethylene.

6. The dressing of claim 1 wherein the casting sheet is constructed of a blend of polypropylene and polyethylene.

7. The dressing of claim 1 wherein the transparent film is moisture vapor permeable.

8. The dressing of claim 1 wherein the transparent film is constructed of polyurethane.

9. The dressing of claim 1 further comprising:

a pattern on the casting sheet.

10. The dressing of claim 1 wherein the gripping strip is constructed of cellophane tape.

11. The dressing of claim 1 wherein the adhesive coating extends from the left edge of the transparent film to the right edge of the transparent film such that the adhesive coating is adjacent to the gripping strip.

12. The dressing of claim 1 further comprising:

information printed on the hinge.

* * * * *